United States Patent [19]

Wedgwood et al.

[11] Patent Number: 4,642,687

[45] Date of Patent: Feb. 10, 1987

[54] SUPERIMPOSITION OF NON-VISUAL SIGNALS UPON AN IMAGE SIGNAL IN A VIDEO DISPLAY SYSTEM

[75] Inventors: Francis A. Wedgwood, Nr Wallingford; Peter F. Peck, Wantage; Michael P. Stevens, Drayton, all of England

[73] Assignee: United Kingdom Atomic Energy Authority, London, England

[21] Appl. No.: 576,939

[22] Filed: Feb. 6, 1984

[30] Foreign Application Priority Data

Feb. 10, 1983 [GB] United Kingdom ................. 8303693

[51] Int. Cl.⁴ .......................... H04N 5/30; H04N 9/04
[52] U.S. Cl. ...................................... 358/110; 358/41; 358/209
[58] Field of Search .................... 358/93, 106, 110, 22, 358/41, 107, 111, 112, 113, 183, 209

[56] References Cited

U.S. PATENT DOCUMENTS

| | | | |
|---|---|---|---|
| 3,465,145 | 9/1969 | Leiter | 358/110 |
| 4,026,144 | 5/1977 | Gericke et al. | 358/82 |
| 4,160,997 | 7/1979 | Schwartz | 358/93 |
| 4,246,607 | 1/1981 | Vijverberg | 358/93 |
| 4,349,739 | 9/1982 | Annis | 358/106 |
| 4,494,001 | 1/1985 | Peck | 250/358.1 |
| 4,509,061 | 4/1985 | Nomoto et al. | 358/112 |

Primary Examiner—James J. Groody
Assistant Examiner—Randall S. Svihla
Attorney, Agent, or Firm—William R. Hinds

[57] ABSTRACT

A signal is generated for producing a video display carrying superimposed images, at least one of which is derived from a system for detection of non-visual signals, such as an ultrasonic inspection device or a backscatter detector of penetrating radiation. Accurate registration of the superimposed images is achieved by providing for the system for detection a moveable probe indicating the location of inspection by the detector system, a point source of light or other radiation to which a video camera responds on the probe which point source is 'on' when the detector response is positive, and a comparator and memory system in which is built up a store of all those image locations where the camera observed the point source 'on'. Output from the memory system is mixed with the camera video signal so that a bright point is produced at each of those locations thereby to produce the superimposed image. By providing a separate memory system for red, green and blue color signals from a color camera, different colored point sources of light may be used to produce a range of superimposed images of different colors.

5 Claims, 4 Drawing Figures

SUPERIMPOSITION OF NON-VISUAL SIGNALS UPON AN IMAGE SIGNAL IN A VIDEO DISPLAY SYSTEM

The invention relates to apparatus for providing a video display in which an image derived from signals from two or more detector systems are superimposed. More particularly the invention relates to apparatus for providing a video display in which an image derived from a detector of, for example, penetrating radiation or from an ultrasonic or like test device, is superimposed upon a visual image derived from a camera.

In this way a user of the apparatus can be assisted by relating the output of a non-visual signal detector device to the visual appearance of the image produced by the camera of an object under test.

Whilst highly sophisticated image processing and handling techniques are available using computers or microprocessors, a problem with the type of image superimposition referred to above is that of registering one image in its proper relationship and scale with the other.

According to the present invention this registration problem is solved by providing apparatus for generating a video display signal capable of driving a suitable imaging system to produce superimposed images from two or more detector systems, in which one or at least one of the detector systems includes a movable probe, a camera, a source on the probe the position of which source is indicative of the position of investigation of the associated detector system, and which source produces light, or other radiation to which the camera responds, in excess of a predetermined intensity whenever the source is energized by the said associated detector system, the camera producing, when trained upon the area of investigation, a video signal including that produced by the said source on the probe, a threshold detector for detecting whenever light or said other radiation received by the camera exceeds the said predetermined intensity, a memory system scanned in synchronism with the camera arranged to store the video signal at all positions where the said predetermined intensity is exceeded, and means for mixing video signals from the memory store with the signals from the camera so that the mixed signals when fed to an imaging system are displayed as the visual image seen by the camera with superimposed bright points at all positions where the said predetermined intensity has been exceeded.

In this way, using a camera which responds to visible light and a light source on the probe, it is possible to scan the probe over an object and build up an array of bright points superimposed upon the ordinary visual image of the object, the bright points corresponding with some predetermined characteristic under investigation. Thus for example, the detector system may be as described in British Patent Specification No. 2055198 in which backscattered penetrating radiation is detected, for example neutrons to reveal low atomic number material concealed behind steel.

It will be appreciated that the camera providing a video signal of the visual scene may be regarded as one detector system, which, together with another detector system including a probe with a light source thereon, will constitute an apparatus comprising two detector systems. Alternatively there may be additional detector systems each including a probe with a light source thereon. In this case it is desirable to distinguish one detector system from another by using different coloured light sources on the probes. Further, the indication of the response of a single detector system may be sub-divided by providing on the probe a plurality of light sources distinguishable from one another by differences in colour. It is also possible for certain applications that display may be wanted of only the images produced by scanning the probes of two or more detectors without including display of the visual scene. In this case the camera would be set to respond only to the brightness of the light sources on the probes and to produce no image from other sources of light.

Specific constructions of apparatus embodying the invention will now be described by way of example and with reference to the drawings filed herewith, in which:

FIG. 1 shows a monochrome system used for superimposing on an image of a visual scene an image produced using a detector of non-visual signals, such as a detector of penetrating radiation.

To illustrate this example, we consider the detector system of British Patent Specification No. 2055198. The probe 5 comprises an isotopic source of penetrating radiation and an annular detector arranged for high efficiency detection of the radiation 6 backscattered from the object 7 under test. The output from the detector is monitored and produces an indication when the level of the penetrating radiation backscattered is sufficient to indicate presence of whatever characteristic is under investigation. Thus, using neutrons as the penetrating radiation, it is possible to detect material containing hydrogen, even although this may be concealed behind steel, for example behind the outer metal skin of a car door.

The probe is modified for the purpose of the present example by mounting a point source 8 of light on the back. This light source is connected to the detection circuitry so as to be on material containing hydrogen is detected.

Figure 1:
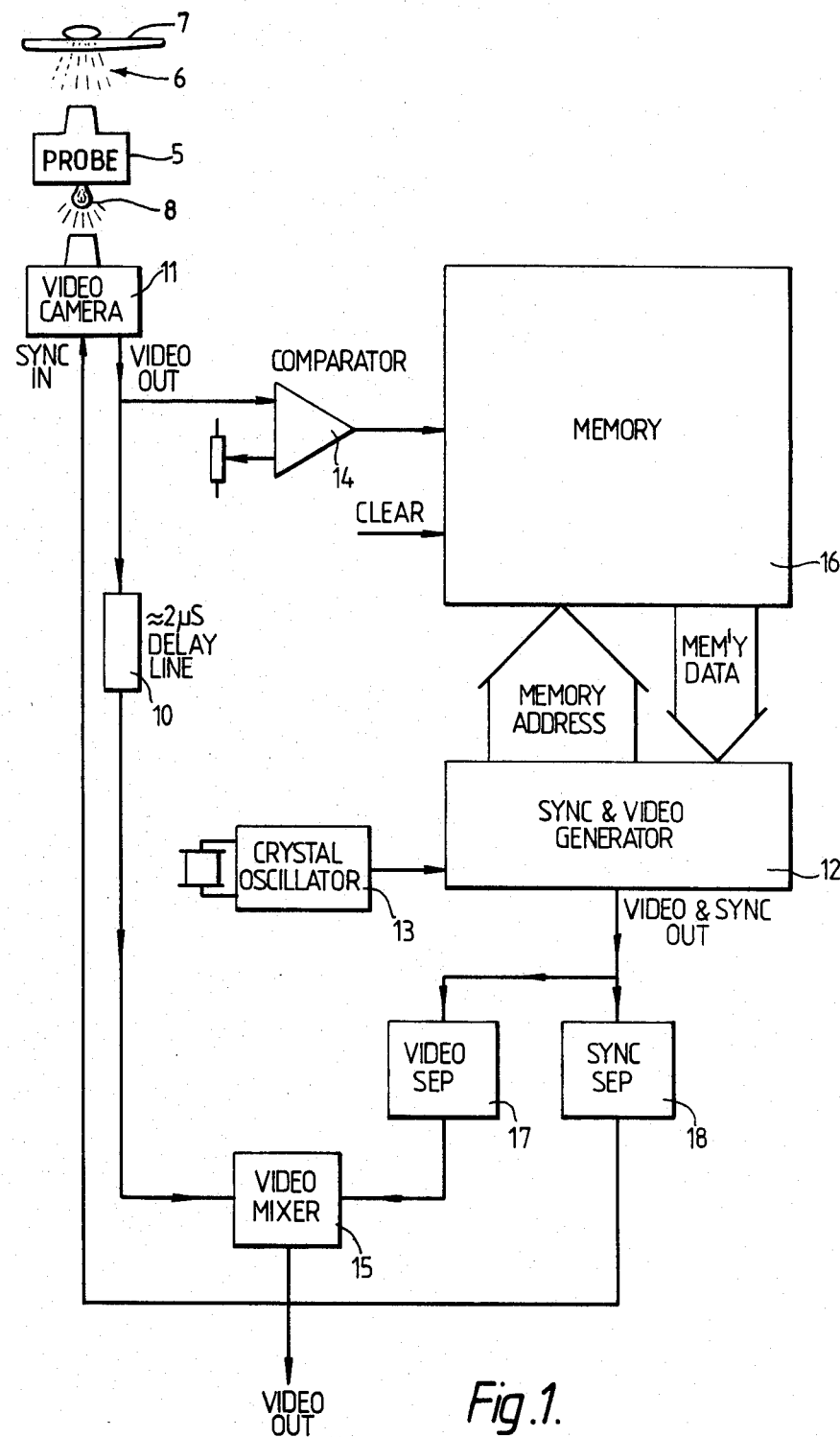
FIG. 1 is a block circuit diagram of part of an apparatus.

Referring to FIG. 1, a video camera 11 is provided with synchronising signals from a generator 12 via sync separator 8 which also generates a video signal as described further below. The operation of the generator 12 is under the time control of a crystal oscillator 13.

Video signal output from the camera 11 is fed to a comparator 14 and also, via a delay line 10 of approximately 2 microseconds delay, to a video mixer 15.

The comparator 14 compares the brightness level of the received video signal with a reference standard and, if this reference standard is exceeded, feeds a signal to memory 16, which is an 8192×8 bit memory with an access time of 35 nanoseconds. Signals from the comparator 14 stored in the memory 16 are coded with a location address based upon the synchronisation signals from the generator 12.

The generator 12 continuously scans the memory 16 and generates a video signal representing the bright points stored and synchronised with the delayed video signal from the camera. The delay line 10 is adjusted to compensate accurately for the delay inherent in the operation of the comparator 14, the memory 16 and the generator 12.

The output from generator 12 comprises a combined video signal (the bright points from the memory 16) and synchronisation signal. These are separated by respectively video separator 17 and sync. separator 18. The sync. signal is fed to the camera 11.

The output from the video mixer 15 comprises a video signal of the image viewed by the camera 11 on which is superimposed an image of all points stored in the memory 16 as having been registered during the scan as exceeding the predetermined brightness level.

This video signal may be converted to a visual image by any suitable imaging system, conveniently a television receiver.

In operation, the probe of the penetrating radiation detector is scanned over the object under test. The light source on the probe comes on as the detector probe passes over, in this example using neutrons, concealed material containing hydrogen. The image locations of all points in the field of view of the camera 11 where the light source comes on are stored so that these points remain continuously bright on the image viewed from the video mixer signal. Thus, by scannning the probe back and forth over the area under search an image is built up of the detected object and this image is seen superimposed upon the direct visual scene observed by the camera.

The scanning of the probe may be carried out manually but is readily adapted for automation.

Figure 2:
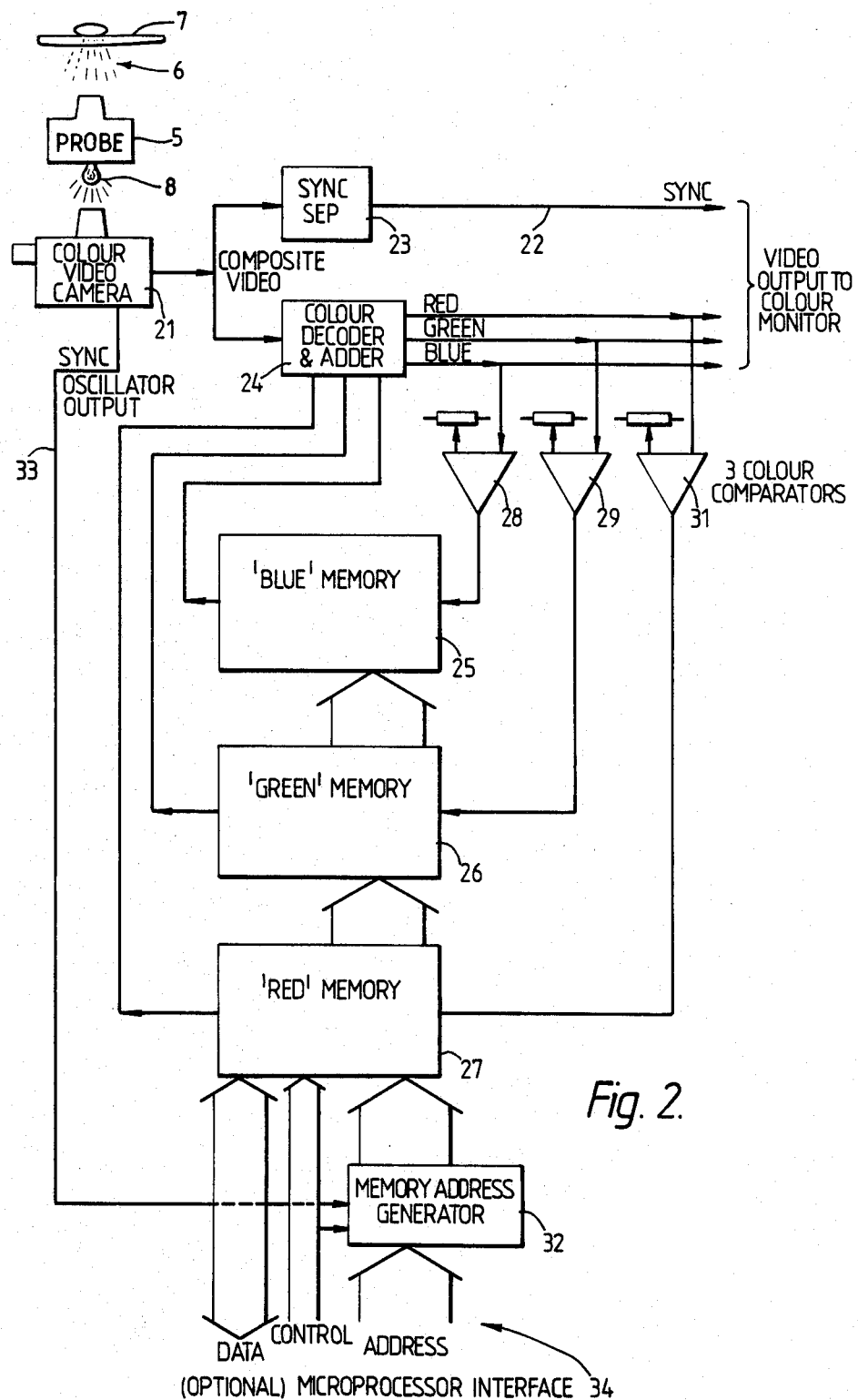
FIG. 2 is a block circuit diagram of part of another apparatus.

If the system is required to operate with more than one detector of non-visual signals, or to provide a different indication for different sub-divisions of the response of one detector, then this can be achieved by a colour system illustrated in FIG. 2.

Referring to FIG. 2, probe 5, object 7, and light source 8 are shown as in FIG. 1. The system is based upon a colour video camera 21, the output from which is a standard composite video signal. From this signal is derived a synchronisation component on line 22 by synchronisation separator 23. The composite video signal is also fed to colour decoder and adder 24 in which the colour signals are separated into their red, green and blue components and added to any signals supplied from the memory stores. The latter comprise "blue" memory 25, "green" memory 26 and "red" memory 27, each being a 16384×8 bit memory.

Three colour comparators 28 (blue), 29 (green), 31 (red), the outputs from which are coupled to the respective memories 25, 26 and 27, compare the respective (blue, green, red) colour intensities with a reference level. When this reference level is exceeded, indicating a bright point in the image, the location address of the bright point is stored in the respective memory (25, 26 or 27). This ensures that the point in the image represented by that address remains bright for all subsequent image scans. The location address for each bright point stored in the memories is set up by a memory address generator 32, synchronisation control for which is provided by the synchronisation output on line 33 from the colour video camera 21.

It will be appreciated that the arrangement shown is readily coupled to a microprocessor if such additional control facility is desired, and the data, control and address connection lines are illustrated schematically at 34. Connection to a microprocessor could provide for processing of the video signal data and/or picture enhancement and/or generation of colour graphics.

The light sources on the detector probes are in different colours but of sufficient brightness in operation to produce outputs from the appropriate colour comparators (28, 29 or 31). Bright points in each colour (red, green or blue) or each colour mix (red-green, red-blue, green-blue, white) thus detected by the comparators are stored in the appropriate memories. As in the FIG. 1 embodiment, the memories are scanned continuously and any points stored are added in the colour decoder and adder 24 to the appropriate colour signals derived direct from the colour video camera 21.

The outputs from the colour decoder and adder 24 together with the synchronisation signal on line 22 provide a drive suitable for connection to a colour monitor.

With an appropriate selection of coloured light sources on the detector probes, the system can be used to provide an image of the visual scene observed by the camera 21 onto which superimposed coloured images can be "painted" in by scanning of the detector probes over the field of view. Each superimposed coloured image will represent the regions of the observed field in which the respective detector gives a positive response. Alternatively a single probe may carry a plurality of light sources each of a different colour, each colour being associated with a sub-division of the response from the detector. The sub-division may be chosen according to the characteristics to be displayed, for example according to the intensity of the detector response, or a depth indication.

Figure 3:
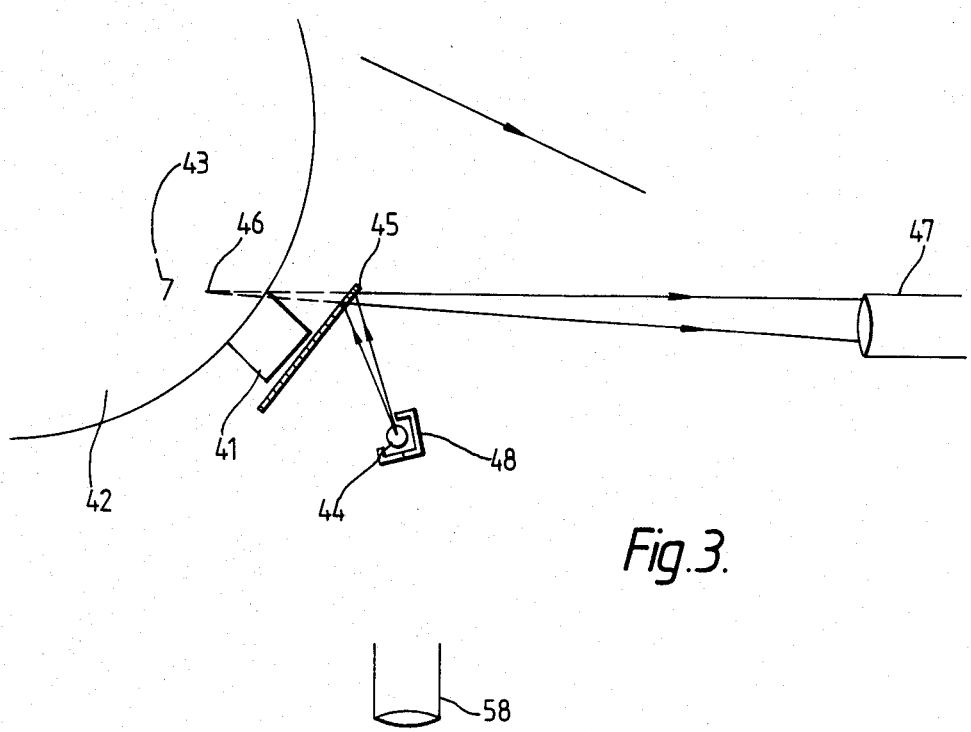
FIG. 3 is a diagrammatic representation of part of an ultrasonic inspection apparatus.

FIG. 3 illustrates an ultrasonic inspection apparatus in which a transducer 41 is coupled to an object 42 for transmission and reception of ultrasonic pulses with the object of discovering defects such as crack 43 by detection of the reflection of the ultrasonic signal by the crack. A point source of light 44 is provided either as a small bulb connected by wire to the test set (not shown) or from an optical fibre connected to a light source on the test set. The source is switched on whenever a reflected signal representing a crack is detected as the transducer 41 is moved over the object 42.

If the light source is mounted on the back of the transducer 41, the spacing from the surface of the object 42 would give rise to parallax errors. This is avoided, in this example, by using a mirror 45 to produce a virtual image at 46, as seen by camera 47. A screen 48 prevents light from the source 44 from passing directly to the camera 47. By appropriate positioning of the source 44 and the mirror 45, or, if necessary, using a lens system or curved mirror, it is possible to locate the virtual image 46 wherever is most suitable. This may be coincident with the surface of the object 42, or, as shown, below the surface a distance which can be arranged to coincide with the depth set for the ultrasonic inspection.

If camera 47 is coupled to apparatus as described with reference to FIG. 2, a further alternative mode of operation provided by the colour system is for the probe to carry a plurality of light sources each of a different colour. These different colour light sources can be arranged to come on according to different characteristics of the response of the associated detector. For example, one colour would represent no response and, as the probe is scanned, would be effectively painted in to show the areas that have been scanned, and another colour would represent a positive response from the detector. Such positive responses could be sub-divided, for example according to intensity, or a depth or distance indication, a different colour light source being associated with each sub-division. In this way scanning would build up a colour map showing the areas of the object from which the various different responses are detected. The plurality of different colour light sources could either be arranged as close as possible to one another or with lens and/or mirror systems to provide virtual sources. The virtual sources could, if desired, then be coincident.

Figure 4:
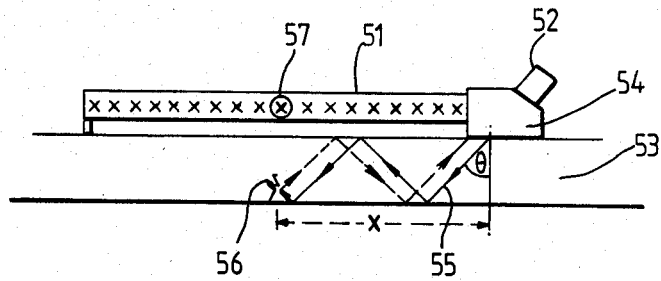
FIG. 4 is a diagrammatic representation of part of another ultrasonic inspection apparatus.

FIG. 4 illustrates an arrangement in which use is made of a luminous location indicator comprising an array 51 of point sources provided by light emitting diodes. An ultrasonic transducer 52 is coupled to an object 53 via a coupling block 54 so as to inject ultrasonic pulses along an angled path 55. The pulses are internally reflected back and forth at the top and bottom surfaces of the object 53. If a crack or other ultrasound reflecting defect is encountered, as at 56, the reflected pulse returns to the transducer via the path shown dotted.

When such a reflected pulse is detected, the electronics is arranged to excite the diode at 57 which is immediately above the defect 56. This is achieved for a parallel sided sheet as shown, if $$x = vt/2 \sin \theta$$

where
  x is the distance of the diode at 57 from the point where the transmitted ultrasonic pulse enters the object 53
  v is the velocity of ultrasound in the object 53
  $\theta$ is the angle of incidence as shown
and
  t is the time elapsed between transmission of the ultrasonic pulse and reception of the echo pulse.

Camera 58 coupled to apparatus as described with reference to FIG. 1 or FIG. 2 will build up an image of the points of light located immediately above defects revealed as the whole device is moved over the object 53.

This form of apparatus shown in FIG. 4 is particularly suitable for the inspection of welds using angled shear waves.

As with the FIG. 3 apparatus, it is possible with the FIG. 4 apparatus to use different colours for sub-dividing the indication detector response. For this, however, each colour would require a linear array of light sources. Clearly, the number of different colours used with a single probe is limited by the practicality of accommodating all the light sources and any associated optical equipment in the space available on a reasonably sized probe.

The invention is not restricted to the details of the foregoing examples. Whilst specific examples of systems for detection of non-visual signals have been mentioned, that is using penetrating radiation, or ultrasound, it will be appreciated that the apparatus can be used with any detector system for which response can be confined to limited areas defined by a probe position or probe and associated point light source position. For example, an eddy current probe can readily be adapted for use in accordance with the invention in a manner analogous to an ultrasonic detection system.

The arrangement is readily adapted for use with a camera which responds to other than visual radiation. Thus, a camera sensitive to infra-red radiation, for example may be used. Where the camera, as is usual, also responds to visible light, an infra-red emitting diode could be used as the source on the probe. The intensity of the infra-red emitted by the diode would have to be such as to exceed a predetermined reference level to produce an output from a comparator as at 14 in FIG. 1. Alternatively, an infra-red camera would clearly enable a general image to be formed of a scene (e.g. at night) which is not illuminated with visible light but which is emitting infra-red. In that case the source on the probe could also be an infra-red emitting diode or alternatively could be a source of visible light.

The mixed video signal output may be recorded on a video recorder for subsequent display via a monitor. The mixed video signal may be transmitted over long distances by cable or radio transmission if desired.

We claim:

1. An apparatus for generating a video display signal capable of driving a suitable imaging system to produce superimposed images from a video camera and one or more detector systems, which apparatus comprises a video camera, one or more detector systems, the one or at least one of the detector systems including a movable probe, a source on the probe, the position of which source is indicative of a position of investigation of the associated detector system, a detection response of the associated detector system energizing the source, which source when energized produces light, or other radiation to which the camera responds, in excess of a predetermined intensity, the camera producing, when trained upon an area including said position of investigation, a video image signal of the area including said light or other radiation from the source on the probe, a threshold detector for detecting whenever said light or said other radiation received by the camera exceeds said predetermined intensity, a memory system scanned in synchronism with the video image signal and arranged to store the video image signal at all image positions where said predetermined intensity is exceeded, and means for mixing a video signal produced by scanning said memory system with the video signal from the camera so that the mixed signal when fed to an imaging system is displayed as a visual image of the area upon which the camera is trained with superimposed bright points at said image positions where said predetermined intensity has been exceeded.

2. An apparatus as claimed in claim 1, in which the camera is a monochrome video camera, and there is only one detector system which includes a movable probe as aforesaid.

3. An apparatus as claimed in claim 1, in which the camera is a colour video camera and a plurality of light sources having different colours are provided on the probe, the colours being selected from red, green and blue or the colour mixes red-green, red-blue, green-blue and white.

4. An apparatus as claimed in claim 1 in which an optical system presents to the camera a virtual image of the source of light or other radiation.

5. An apparatus as claimed in claim 1, in which a plurality of sources of light or other radiation are associated with each probe, a detection response of the associated detector system energizing a selected source, the position of which selected source indicates a position of investigation of the detector system.

* * * * *